United States Patent [19]

Harris

[11] Patent Number: 4,533,759

[45] Date of Patent: Aug. 6, 1985

[54] PROCESS FOR THE PRODUCTION OF FRAGRANCE QUALITY ETHYLENE GLYCOL MONOARYL ETHERS

[75] Inventor: Eugene G. Harris, West Chester, Ohio

[73] Assignee: National Distillers and Chemical Corporation, New York, N.Y.

[21] Appl. No.: 628,557

[22] Filed: Jul. 6, 1984

Related U.S. Application Data

[63] Continuation-in-part of Ser. No. 367,128, Apr. 9, 1982, abandoned.

[51] Int. Cl.$^3$ .................. C07C 41/34; C07C 41/03
[52] U.S. Cl. .................................. 568/648; 568/654
[58] Field of Search ............................. 568/648, 654

[56] References Cited

U.S. PATENT DOCUMENTS

| | | | |
|---|---|---|---|
| 1,944,958 | 1/1934 | Valik et al. | 568/810 |
| 2,944,087 | 7/1960 | Nommensen et al. | 568/914 |
| 3,644,534 | 2/1972 | Reabe et al. | 568/648 |
| 3,646,227 | 2/1972 | Grinstein | 568/914 |
| 3,865,880 | 2/1975 | Quelly et al. | 568/914 X |
| 4,390,732 | 6/1983 | Merk et al. | 568/648 |

FOREIGN PATENT DOCUMENTS

| | | | |
|---|---|---|---|
| 1133556 | 7/1962 | Fed. Rep. of Germany . | |
| 981965 | 2/1965 | United Kingdom | 568/914 |

OTHER PUBLICATIONS

Brochure published by Ventron Corporation, Chemicals Division, "Hydride Chemicals for Process Stream Purification", 10, 11.

*Primary Examiner*—Bernard Helfin
*Attorney, Agent, or Firm*—Kenneth D. Tremain; Gerald A. Baracka

[57] ABSTRACT

Ethylene glycol monoaryl ethers useful as fragrance chemicals are obtained by ethoxylating a phenol in the presence of an alkali metal borohydride and alkali metal hydroxide and neutralizing the resulting monoethoxylated product to pH 6.5–7.5 with an aliphatic di- or polycarboxylic acid or hydroxyaliphatic carboxylic acid. Ethylene glycol monophenyl ether having a consistent mild rose odor profile and free of undesirable metallic notes is obtained by the present process.

9 Claims, No Drawings

PROCESS FOR THE PRODUCTION OF FRAGRANCE QUALITY ETHYLENE GLYCOL MONOARYL ETHERS

CROSS-REFERENCE TO RELATED APPLICATION

This is a continuation-in-part of copending application Ser. No. 367,128, filed Apr. 9, 1982.

BACKGROUND OF THE INVENTION

1 Field of the Invention

The present invention relates to an improved process for the monoethoxylation of phenols whereby fragrance quality ethylene glycol monoaryl ethers, such as ethylene glycol monophenyl ether, are produced.

2. Description of the Prior Art

Ethylene glycol monoaryl ethers are known. These compounds are usually obtained by reacting phenol with ethylene oxide in the presence of an alkaline catalyst. Processes utilizing a variety of basic catalysts such as ammonia, urea, amides, hydroxides and phenates of sodium and lithium, potassium hydroxide and the like are described in U.S. Pat. Nos. 2,852,566; 3,354,227; 3,364,267; 3,525,773; 3,642,911 and 3,644,534.

Whereas products obtained by such processes are suitable for most commercial applications they are not completely acceptable for use in cosmetic preparations and fragrance formulations due to the presence of an objectionable pungent "metallic" odor. Ethylene glycol monophenyl ether obtained by such processes, for example, cannot be utilized in cosmetic preparations or as a solvent and fixative for perfumes without further purification since the undesirable metallic note masks the pleasant odor of the ethylene glycol monophenyl ether and any other fragrance chemicals employed therewith. Even when the ethylene glycol monophenyl ether is carefully distilled after ethoxylation to obtain high purity water-white product essentially free of catalyst residue, unreacted phenol and higher ethylene oxide adducts, the undesirable metallic note is still not completely removed.

In U.S. Pat. No. 4,404,407 a post-treatment procedure whereby ethylene glycol monophenyl ether is contacted with sodium borohydride to eliminate the undesirable metallic note and thus obtain a highly useful fragrance grade ethylene glycol monophenyl ether is disclosed. Treating with sodium borohydride also generally obviates the need for distilling the product.

The post-treatment of polyethoxylated products (having 3 to 80 moles ethylene oxide condensed therewith) with sodium borohydride to improve color is reported in the technical literature of Ventron Corporation Chemicals Division in a brochure entitled "Hydride Chemicals for Process Stream Purification". It is also suggested that another method of treatment of the polyethoxylates would be to add the sodium borohydride with the caustic used as a catalyst for the condensation to prevent the darkening that normally occurs during reaction. A similar procedure is suggested for the production of ethoxylated fatty alcohol surfactants in PROCESS STREAM PURIFICATION NEWSLETTER, December 1979, Issue No. 3, published by Thiokol/Ventron Division. All of the above procedures deal with the treatment or manufacture of polyethoxylates and there is no indication that fragrance quality ethylene glycol monoaryl ethers be obtained by similar methods.

SUMMARY OF THE INVENTION

I have now unexpectedly discovered that high quality fragrance grade ethylene glycol monoaryl ethers can be obtained by monoethoxylating a phenol in the presence of alkali metal hydroxide and alkali metal borohydride, adjusting the pH of the resulting monoethoxylate to 6.5 to 7.5 by the addition of an aliphatic di- or polycarboxylic acid or hydroxyaliphatic carboxylic acid, and removing any insoluble materials.

The improved process of this invention involves reacting essentially one molar equivalent ethylene oxide with a phenol to which has been added from 0.01 to 1 weight percent alkali metal hydroxide and 0.01 to 1 weight percent alkali metal borohydride. Phenols employed in the process correspond to the formula

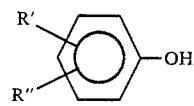

where R' and R" are hydrogen or an alkyl, alkenyl or alkoxyl group having from 1 to 8 carbon atoms. The process is particularly adaptable for use with phenol and monosubstituted phenols wherein the substituent has from 1 to 4 carbon atoms. Most generally, 0.05 to 0.5 weight percent lithium hydroxide, sodium hydroxide or potassium hydroxide are employed with 0.05 to 0.5 weight percent sodium borohydride. Preferably the monoethoxylation is carried out at a temperature from 110° C. to 130° C. and pressure from about 1 psi to 50 psi.

The pH of the ethylene glycol monoaryl ether is adjusted to about pH 6.5-7.5 by the addition of a suitable carboxylic acid thereto. Carboxylic acids useful for this purpose include aliphatic di- and polycarboxylic acids having from 3 to 16 carbon atoms and hydroxyaliphatic carboxylic acids having from 2 to 8 carbon atoms. Upon neutralization, these carboxylic acids form salts which are insoluble in the ethylene glycol monoaryl ether product and which therefore may be readily removed by filtration. The ethylene glycol monoaryl ethers may also be steam sparged to further improve their quality and obtain products having consistent odor profiles and which are essentially free of any metallic odor. For the steam sparging up to about 10 wt. percent water is introduced subsurfacely and dispersed into the ethylene glycol monoaryl which is maintained at an elevated temperature and reduced pressure. Most generally, 0.5 to 5 wt. percent water is employed for the sparging while maintaining the ethylene glycol monoaryl ether at a temperature of 75° C. to 120° C. and pressure less than 100 mm Hg. The improved process of this invention is particularly useful for the preparation of ethylene glycol monophenyl ether useful in cosmetic and fragrance applications.

DETAILED DESCRIPTION

The improved process of this invention for the preparation of ethylene glycol monoaryl ethers comprises combining an alkali metal hydroxide and alkali metal borohydride with a phenol and then reacting with essentially one molar equivalent ethylene oxide. The resulting ethylene glycol monoaryl ether is then neutralized with a carboxylic acid and filtered to remove insoluble acid salts which are formed. In yet another embodiment, the process involves the additional step of sparging the ethylene glycol monoaryl ether with steam.

Phenol or various substituted-phenols can be monoethoxylated in accordance with the procedure of this invention. The phenols typically correspond to the formula

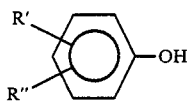

wherein R' and R" are hydrogen or an alkyl, alkenyl, or alkoxyl group having from 1 to 8 carbon atoms. Especially useful in the process are phenol and monosubstituted phenols wherein the substituent contains from 1 to 4 carbon atoms. It should be noted that phenols having substituents in the ortho ring position will react more slowly than other substituted phenols. Illustrative phenols which can be monoethoxylated in accordance with this invention are phenol, cresol, ethyl phenol, methoxy phenol, t-butyl phenol, di-methyl phenol, chavicol and the like.

For the process, 0.01 weight percent up to 1 weight percent, based on phenol, alkali metal hydroxide and 0.01 to 1 weight percent, based on phenol, alkali metal borohydride are combined with the phenol prior to introducing the ethylene oxide. The alkali metal borohydride preferably employed is sodium borohydride, however, other alkali metal borohydrides such as lithium borohydride and potassium borohydride can also be utilized in the process. Most preferably, 0.05 to 0.5 weight percent alkali metal hydroxide and 0.05 to 0.5 weight percent sodium borohydride are utilized. Suitable alkali metal hydroxides include lithium hydroxide, sodium hydroxide and potassium hydroxide.

To facilitate addition of the alkali metal hydroxide and alkali metal borohydride, the phenol is maintained in a molten state. The temperature of the phenol can be any temperature above its melting point up to the temperature at which the ethoxylation reaction is to be carried out. In the usual practice of the invention the alkali metal hydroxide and sodium borohydride are charged to the reactor containing the phenol while it is being raised to the reaction temperature.

The alkali metal hydroxide and sodium borohydride may be added in any order or they may be added simultaneously. The exact nature of the resulting specie is not known, however, it is believed to be a mixture of alkali metal and boron phenolates which results from the reaction/interaction of the alkali metal borohydride with phenol.

The ethoxylation reaction is typically being carried out at a temperature from about 100° C. to 150° C. and, more usually, from 110° C. to 130° C. Whereas the reaction can be carried out at atmospheric pressure or at superatmospheric pressures up to 1000 psi or higher, most generally the pressure is between about 1 psi and about 50 psi.

To obtain the ethylene glycol monoaryl ethers one molar equivalent ethylene oxide is then reacted with the phenol. The ethylene oxide can be added to the phenol as a liquid or as a gas, however, to maximize the yield of monoethoxylate and minimize the formation of higher ethoxylation products no more than 10 percent molar excess should be charged if a closed system is employed. Preferably, less than 5 percent molar excess ethylene oxide will be present. While some water can be present in the reaction mixture it is preferred that the amount of water be kept as low as possible. Ethylene oxide addition is maintained at a rate such that the reaction exotherm can be controlled and so that a large excess of ethylene oxide is not present in the reactor at any time during the course of the reaction. An external cooling source will typically be required to maintain the reaction temperature within acceptable limits. The reaction time is primarily dependent on the temperature of the reaction and the particular phenol being used. The reaction is terminated when essentially one molar equivalent ethylene oxide has been reacted or all the phenol has been ethoxylated. This is accomplished by simply cooling the reaction mixture and venting any excess ethylene oxide from the reactor.

The general procedure for conducting the reaction consists of charging the phenol to a reactor with agitation. For ease of handling the phenol is usually charged in a molten state, however, this is not necessary. Heating is then begun and the alkali metal hydroxide and sodium borohydride charged. The mixture is usually agitated and sparged with nitrogen while pulling a vacuum to facilitate removal of gases being evolved. When gas evolutuion is essentially complete, the mixture is brought to the reaction temperature and ethylene oxide charged. The reaction is maintained at the desired temperature until one molar equivalent of the ethylene oxide has reacted with the phenol. Whereas the process is typically carried out in the above manner as a batch reaction, with suitable equipment and modification it can also be performed on a semicontinuous or continuous basis.

Ethylene glycol monoaryl ethers produced by the above procedure may be used as such for some general applications without further purification. For example, these products are suitable for use in some preservative and textile applications and are acceptable for further reaction with various carboxylic acids for the preparation of esters. Ethylene glycol monophenyl ether obtained by the above process has markedly improved odor characteristics as compared to product prepared under similar conditions without the addition of sodium borohydride to the reaction. This is quite surprising in view of the fact that the color of both products can be essentially the same.

In spite of the much improved odor of products obtained when sodium borohydride is employed with the alkali metal hydroxide, where the product is to be used for cosmetic and fragrance applications, it has been found to be advantageous to further treat the product in order to obtain ethylene glycol monoaryl ethers, and particularly ethylene glycol monophenyl ether, having consistent odor profiles with no trace of undesirable metallic odor.

To obtain ethylene glycol monoaryl ethers having consistent odor profiles and no undesirable metallic odor, the pH of the product is adjusted using specific carboxylic acids which form salts which are insoluble in the ethylene glycol monoaryl ether and which therefore can be readily removed by filtration, decantation or the like. The removal of the insoluble salts also enhances the heat stability of the resulting products.

Ethylene glycol monoaryl ethers obtained by the aforementioned procedure, and which typically have a pH of 9 or above, are neutralized to pH 6.5–7.5 by the addition of an appropriate amount of an aliphatic di- or polycarboxylic acid or hydroxyaliphatic carboxylic acid. Aliphatic di- and polycarboxylic acids useful for the process of this invention are saturated acids containing from 3 to 16 and, more preferably, 6 to 12 carbon atoms. Hydroxyaliphatic carboxylic acids which can be utilized are saturated acids having from 2 to 8 carbon atoms and, more preferably, from 2 to 6 carbon atoms. Illustrative carboxylic acids of the above types include malonic acid, succinic acid, glutaric acid, adipic acid, pimelic acid, suberic acid, azelaic acid, sebacic acid, dodecanedioic acid, citric acid, tartaric acid, glycolic acid, lactic acid, and the like. The aliphatic carboxylic acids may contain from two to four carboxyl groups and the hydroxyaliphatic carboxylic acids can have from one to three carboxyl groups and one or two hydroxyl groups. Hydroxyaliphatic acids (citric, tartaric, glycolic and lactic) are particularly desirable for the process of this invention since they form crystalline salts which can be easily separated from the ethylene glycol monoaryl ether product. Citric acid is especially useful for the production of fragrance quality ethylene glycol monophenyl ether having a pleasant mild rose odor.

In an especially useful embodiment of this invention, the product is sparged with steam after neutralization and before removal of the insoluble salts. Steam sparging is accomplished by subsurfacely introducing and dispersing up to 10 wt. percent water into the product which is maintained at a temperature from 75° C. to 120° C. and at a pressure less than 100 mm Hg. The water is introduced into the product through a sparge ring or other suitable apparatus. Preferably from 0.5 to 5 weight percent water is employed and the sparging operation is carried out at a temperature from 90° C. to 110° C. and pressure less than 50 mm Hg. After the desired amount of water has been introduced, the product is then dried to the desired moisture level—usually less than 1 percent and, more preferably, less than 0.5 percent. This is typically accomplished by maintaining the vacuum and heating after the addition of water has been discontinued. A dry inert gas, such as nitrogen, may be passed through the product to facilitate removal of the water during the drying operation. When the desired moisture content is achieved, the ethylene glycol monoaryl ether is filtered or otherwise treated to remove the insoluble salts present therein. It is also possible to carry out the filtration, i.e., remove the insoluble salts, prior to the steam sparging operation.

The invention is more fully illustrated by the following examples:

EXAMPLE I

Phenol was heated to 60° C. under nitrogen and charged to a standard ethoxylation kettle. After sparging the phenol with nitrogen, 0.1 weight percent potassium hydroxide and 0.1 weight percent sodium borohydride were added to the phenol. A vacuum was applied to the reactor and when a vacuum of 30 mm Hg could be maintained the reactor was sealed, heated to 110° C. and ethylene oxide added. The rate of addition of ethylene oxide was controlled to achieve a maximum pressure of 25 psig while maintaining the temperature at 120° C. to 130° C. with full cooling. The reaction mixture was continuously sampled and when the phenol content reached 500 ppm, ethylene oxide addition was terminated, the reactor cooled to under 100° C. and vented. The resulting product which contained 94% monoethoxylate (ethylene glycol monophenyl ether) had a pH of 10.5 and color of 98/100 (percent transmittance measured at 440 and 550 m$\mu$). The product had a pleasant mild rose odor and there was no detectable metallic odor associated with the product.

EXAMPLE II

The above Example was repeated omitting the sodium borohydride. Potassium hydroxide was added to the phenol at a 0.2 weight percent level. The ethoxylation was accomplished without difficulty but at a somewhat slower rate. The final product had a color of 76/94 (percent transmittance measured at 440 and 550 m$\mu$) and contained 90% monoethoxylate (ethylene glycol monophenyl ether). There was, however, a harsh pungent metallic odor associated with the product which essentially masked the subtle rose notes of the ethylene glycol monophenyl ether.

EXAMPLE III

To demonstrate the ability to enhance the desirable fragrance characteristics of products obtained by the process of this invention and to obtain an essentially neutral product suitable for use in cosmetic and fragrance applications, the ethylene glycol monophenyl ether product obtained by the process of Example I was neutralized to a pH of 7 by the addition of 50% aqueous citric acid solution and then steam sparged. Steam sparging was accomplished by heating to 115° C. while adding 1.5 weight percent water through a sparge ring in the bottom of the reactor. The rate of addition was controlled so that a vacuum of 60 mm Hg was maintained. When water addition was complete, the heating was continued while maintaining a vacuum until the water content was less than 0.2 weight percent. The product was cooled and filtered to remove insoluble salts formed as a result of the neutralization. The ethylene glycol monophenyl ether (boiling point 245° C.) contained 94% monoethoxylate and had no measurable phenol content. The resulting product had a pleasant mild rose odor with subtle fresh green nuances and was a highly useful and desirable extender for the rose note of phenethyl alcohol in various fragrance formulations. For example, formulating 5 parts phenethyl alcohol, 2 parts d-citronellol, 2 parts l-citronellol, 5 parts geraniol and 1.5 parts of the ethylene glycol monophenyl ether yields a fragrance having excellent rose notes. Ethylene glycol monophenyl ether produced in the above manner consistently had the same odor profile.

EXAMPLE IV

Ethylene glycol monophenyl ether containing 96% monoethoxylate and 0.05% phenol was obtained following the procedure of Example I. Samples of the ethylene glycol monophenyl ether thus produced (pH 11.8) were neutralized with various aliphatic dicarboxylic acids and hydroxyaliphatic acids as follows:

| Acid | Final pH |
| --- | --- |
| Malonic acid | 6.68 |
| Adipic acid | 7.17 |
| Azelaic acid | 7.06 |
| Dodecanedioic acid | 6.84 |
| Hexadecandioic acid | 7.07 |
| Glycolic acid | 7.05 |
| Citric acid | 6.41 |

Insoluble salts were formed during the neutralization with all of the above acids. The neutralized products were then steam sparged with about 1.5 weight percent water in accordance with the usual procedure. After drying to a moisture content of less than 0.2%, the products were filtered to remove the insoluble precipitates and the ethylene glycol monophenyl ether recovered. In all instances the odor of the resulting ethylene glycol monophenyl ether product was consistent with the product of Example III, i.e., mild rose odor with fresh green nuances, and was significantly improved over that of the starting material.

EXAMPLE V

To demonstrate the superiority of ethylene glycol monophenyl ether neutralized with aliphatic dicarboxylic acids and hydroxyaliphatic acids versus product neutralized with monocarboxylic acids, the following comparison was carried out. The ethylene glycol monophenyl ether employed for the comparison was prepared in accordance with the procedure of Example I and had a pH of about 10.5. The material had a color of 94/96 (percent transmittance measured at 440 and 550 ml) and had a pleasant mild rose odor. The pH of the product was then adjusted to between 6.5-7 using various acids. Odor and color of the neutralized product was then determined after heating at 205° C. for one hour. Results are set forth in the table below. In the table "+" indicates that no undesirable maladorous constituents were detected and that the product, after heating, had essentially the same odor profile as the staring material. The presence of undesirable off-notes is indicated by "—".

| Neutralizing Agents | Odor | Color |
| --- | --- | --- |
| Formic acid | — | 29/69 |
| Propionic acid | — | 72/90 |
| Pelargonic acid | — | 56/83 |
| Stearic acid | — | 67/88 |
| Oxalic acid | + | 45/80 |
| Malonic acid | + | 67/88 |
| Tartaric acid | + | 77/91 |
| Citric acid | + | 77/93 |
| Glyoxylic acid | + | 75/90 |

It is apparent from the above comparison that the thermal stability of the product obtained in accordance with the present invention is substantially superior to product obtained after neutralization with monocarboxylic acids. Only when the neutralization is carried out using aliphatic dicarboxylic acids or hydroxyaliphatic acids is it possible to retain both acceptable odor and color in the ethylene glycol monophenyl ether product.

EXAMPLE VI

The following comparative experiments demonstrate the ability to obtain improved rates of reaction by the process of this invention. For this example two experiments were carried out reacting 300 gms phenol with 157 gms ethylene oxide at 125°-135° C. and 30-40 psig. For the first reaction (identified as Run A) 0.9 gm potassium hydroxide and 0.9 gm sodium borohydride were added to the phenol in accordance with the process of this invention prior to carrying out the ethoxylation and in the second reaction (identified as Run B) only potassium hydroxide (1.82 gms) was added to the phenol. For Run A, reaction with ethylene oxide was complete in 45 minutes and the resulting product was devoid of any metallic odor. Sixty minutes were required to complete the ethoxylation for Run B and the resulting product had a severe metallic odor. The marked superiority of the odor qualities of the ethylene glycol monophenyl ether obtained from Run A was quite surprising in view of the fact that both products had essentially the same color.

EXAMPLE VII

In accordance with the previously described procedures 300 gms p-methoxyphenol, 0.67 gm potassium hydroxide and 0.70 gm sodium borohydride were charged to an autoclave. Ethylene oxide was then added over a 2½ hour period while maintaining the temperature at 130°-140° C. and pressure in the range 30-40 psig. When the ethylene oxide addition was complete heating was continued at 135° C. for 30 minutes. There was no trace of undesirable metallic odor in the resulting product which was confirmed by chromatographic analysis to contain 95.2% monoethoxylated product.

I claim:

1. An improved process for the preparation of ethylene glycol monoaryl ethers which comprises combining 0.01 to 1.0 wt. percent alkali metal hydroxide and 0.01 to 1 weight percent alkali metal borohydride with a phenolic compound of the formula

where R' and R" are hydrogen or an alkyl, alkenyl or alkoxyl group having from 1 to 8 carbon atoms, said phenol maintained at a temperature above its melting point, reacting with essentially one molar equivalent ethylene oxide at a temperature from 100° C. to 150° C. and pressure from atmospheric up to 1000 psi, neutralizing to a pH of 6.5-7.5 with an aliphatic di- or higher polycarboxylic acid or hydroxyaliphatic carboxylic acid and removing any insoluble salts.

2. The process of claim 1 wherein the alkali metal borohydride is sodium borohydride, the alkali metal hydroxide and sodium borohydride are both utilized in amounts from 0.05 to 0.5 weight percent, based on the phenol, and the phenolic compound is phenol or a monosubstituted phenol wherein the substituent contains from 1 to 4 carbon atoms.

3. The process of claim 2 wherein the alkali metal hydroxide is potassium hydroxide and the ethoxylation is carried out at a temperature from 110° C. to 130° C. and pressure between about 1 psi and 50 psi.

4. The process of claim 3 wherein the aliphatic di- or polycarboxylic acid is a saturated acid having from 3 to 16 carbon atoms and the hydroxyaliphatic carboxylic acid is a saturated acid having from 2 to 8 carbon atoms.

5. The process of claim 4 wherein the hydroxyaliphatic carboxylic acid is selected from the group consisting of citric acid, lactic acid, glycolic acid or tartaric acid.

6. The process of claims 1, 2, 3, 4 or 5 comprising the further steps of sparging the ethylene glycol monoaryl ether by subsurfacely introducing and dispersing up to 10 weight percent water therein at a temperature of 75° C. and 120° C. and pressure less than 100 mm Hg and drying to a moisture content less than 1 percent.

7. The process of claim 6 wherein the sparging is carried out at a temperature of 90° C. to 110° C. and pressure less than 50 mm Hg utilizing from 0.5 to 5 weight percent water.

8. The process of claim 7 wherein the ethylene glycol monoaryl ether is ethylene glycol monophenyl ether.

9. The process of claim 8 wherein the sparging is carried out after the neutralization and before removal of the insoluble salts.

* * * * *